United States Patent
Kwok et al.

(10) Patent No.: US 10,342,941 B2
(45) Date of Patent: Jul. 9, 2019

(54) METHODS AND APPARATUS FOR CONTROLLING MASK LEAK IN CPAP TREATMENT

(71) Applicant: ResMed Pty Ltd, Bella Vista, New South Wales (AU)

(72) Inventors: Philip Rodney Kwok, Sydney (AU); Ron Richard, Escondido, CA (US); Karthikeyan Selvarajan, Sydney (AU); Glenn Richards, Auckland (NZ); Nicholas Jerome Reed, Sydney (AU); Larry Puckeridge, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 1262 days.

(21) Appl. No.: 14/298,115

(22) Filed: Jun. 6, 2014

(65) Prior Publication Data
US 2014/0283836 A1     Sep. 25, 2014

Related U.S. Application Data

(63) Continuation of application No. 11/921,753, filed as application No. PCT/AU2006/000823 on Jun. 14, 2006, now Pat. No. 8,789,526.

(30) Foreign Application Priority Data

Jun. 14, 2005  (AU) ............................... 2005903089
Nov. 4, 2005   (AU) ............................... 2005906122
(Continued)

(51) Int. Cl.
*A61M 16/00*    (2006.01)
*A61B 5/0476*   (2006.01)
(Continued)

(52) U.S. Cl.
CPC ....... *A61M 16/0069* (2014.02); *A61B 5/0476* (2013.01); *A61B 5/087* (2013.01);
(Continued)

(58) Field of Classification Search
CPC .. A61M 16/0069; A61M 16/06; A61M 16/00; A61M 16/0066; A61M 16/0605;
(Continued)

(56) References Cited

U.S. PATENT DOCUMENTS 4,944,310 A     7/1990  Sullivan
5,199,424 A *   4/1993  Sullivan ................ A61B 5/097
                                                128/204.18
(Continued)

FOREIGN PATENT DOCUMENTS

AU          703829       6/1996
EP      0 651 971 A1     5/1995
(Continued)

OTHER PUBLICATIONS

Further Examination Report dated Aug. 3, 2015 issued in European Application No. 06 752 607.9 (4 pages).
(Continued)

*Primary Examiner* — Bradley J Osinski
*Assistant Examiner* — Nilay J Shah
(74) *Attorney, Agent, or Firm* — Nixon & Vanderhye P.C.

(57) ABSTRACT

A method of operating a device for treating sleep disordered breathing (SDB), wherein the device provides continuous positive airway pressure during sleep, includes determining whether treatment pressure at the patient interface is below a desired value, in response to the determining, increasing pressure generated by the flow generator, in response to the increasing, making a determination that the increase in flow generator pressure has resulted in less than a desired increase in treatment pressure at the patient interface, and in
(Continued)

response to the determination, reducing or inhibiting further increase of the flow generator pressure.

42 Claims, 3 Drawing Sheets

(30) Foreign Application Priority Data

| | | |
|---|---|---|
| Nov. 8, 2005 | (AU) | 2005906193 |
| Feb. 16, 2006 | (AU) | 2006900774 |

(51) Int. Cl.

| | |
|---|---|
| *A61B 5/087* | (2006.01) |
| *A61B 5/00* | (2006.01) |
| *A61M 16/06* | (2006.01) |
| *A61M 16/08* | (2006.01) |

(52) U.S. Cl.
CPC .......... *A61B 5/4812* (2013.01); *A61B 5/4818* (2013.01); *A61B 5/4836* (2013.01); *A61M 16/0003* (2014.02); *A61M 16/0051* (2013.01); *A61M 16/0666* (2013.01); *A61M 16/0875* (2013.01); *A61M 16/06* (2013.01); *A61M 16/0605* (2014.02); *A61M 2016/0021* (2013.01); *A61M 2016/0027* (2013.01); *A61M 2016/0036* (2013.01); *A61M 2205/13* (2013.01); *A61M 2205/15* (2013.01); *A61M 2205/502* (2013.01); *A61M 2205/52* (2013.01)

(58) Field of Classification Search
CPC .. A61M 2016/0036; A61M 2016/0039; A61M 2205/15
USPC ............ 128/204.18, 204.21, 204.22, 204.23, 128/204.24, 204.26, 205.25, 206.21
See application file for complete search history.

(56) References Cited

U.S. PATENT DOCUMENTS

| | | | | |
|---|---|---|---|---|
| 5,239,995 | A * | 8/1993 | Estes | A61M 16/00 128/204.18 |
| 5,245,995 | A | 9/1993 | Sullivan et al. | |
| 5,458,137 | A * | 10/1995 | Axe | A61F 5/56 128/204.21 |
| 5,490,502 | A * | 2/1996 | Rapoport | A61B 5/0002 128/204.21 |
| 5,522,382 | A | 6/1996 | Sullivan et al. | |
| 5,551,419 | A * | 9/1996 | Froehlich | A61M 16/0069 128/204.23 |
| 5,632,269 | A * | 5/1997 | Zdrojkowski | A61M 16/0051 128/204.21 |
| 5,645,053 | A * | 7/1997 | Remmers | A61M 16/00 128/204.21 |
| 5,704,345 | A | 1/1998 | Berthon-Jones | |
| 5,803,066 | A * | 9/1998 | Rapoport | A61B 5/0002 128/204.21 |
| 5,823,187 | A | 10/1998 | Estes et al. | |
| 5,901,704 | A | 5/1999 | Estes et al. | |
| 6,029,665 | A | 2/2000 | Berthon-Jones | |
| 6,112,746 | A | 9/2000 | Kwok et al. | |
| 6,138,675 | A | 10/2000 | Berthon-Jones | |
| 6,152,129 | A * | 11/2000 | Berthon-Jones | A61M 16/00 128/200.24 |
| 6,257,234 | B1 * | 7/2001 | Sun | A61M 16/0051 128/204.18 |
| 6,332,463 | B1 | 12/2001 | Farrugia et al. | |
| 6,357,441 | B1 | 3/2002 | Kwok et al. | |
| 6,363,933 | B1 | 4/2002 | Berthon-Jones | |
| 6,398,739 | B1 | 6/2002 | Sullivan et al. | |
| 6,425,395 | B1 | 7/2002 | Brewer et al. | |
| 6,502,572 | B1 | 1/2003 | Berthon-Jones et al. | |
| 6,581,602 | B2 | 6/2003 | Kwok et al. | |
| 6,634,358 | B2 | 10/2003 | Kwok et al. | |
| 6,635,021 | B1 | 10/2003 | Sullivan et al. | |
| 7,013,892 | B2 | 3/2006 | Estes et al. | |
| 7,100,608 | B2 | 9/2006 | Brewer et al. | |
| 8,567,398 | B2 * | 10/2013 | Truschel | A61M 16/12 128/200.24 |
| 2002/0014240 | A1 * | 2/2002 | Truschel | A61M 16/00 128/204.22 |
| 2002/0056452 | A1 * | 5/2002 | Brewer | A61M 16/00 128/202.22 |
| 2003/0066528 | A1 * | 4/2003 | Hill | A61M 16/026 128/204.18 |
| 2004/0016433 | A1 * | 1/2004 | Estes | A61M 16/024 128/204.21 |
| 2005/0085799 | A1 * | 4/2005 | Luria | A61B 5/6803 606/1 |
| 2006/0272645 | A1 | 12/2006 | Ging et al. | |
| 2007/0142741 | A1 | 6/2007 | Berthon-Jones et al. | |
| 2008/0091117 | A1 | 4/2008 | Choncholas et al. | |
| 2008/0163872 | A1 * | 7/2008 | Negele | A61M 16/024 128/204.21 |
| 2009/0078256 | A1 | 3/2009 | Armitstead et al. | |
| 2010/0180895 | A1 | 7/2010 | Kwok et al. | |
| 2011/0100365 | A1 | 5/2011 | Wedler et al. | |
| 2011/0155133 | A1 * | 6/2011 | Barnes | A61M 16/00 128/204.21 |
| 2011/0197886 | A1 | 8/2011 | Guttmann et al. | |

FOREIGN PATENT DOCUMENTS

| | | |
|---|---|---|
| EP | 0 788 805 A2 | 8/1997 |
| JP | 2001-525706 | 12/2001 |
| JP | 2002-532207 | 10/2002 |
| WO | 98/52467 | 11/1998 |
| WO | WO 00/37135 | 6/2000 |
| WO | 2001/97893 | 12/2001 |

OTHER PUBLICATIONS

International Search Report for PCT/AU2006/000823 dated Aug. 25, 2006.
International Preliminary Report on Patentability for PCT/AU2006/000823 dated Dec. 17, 2007.
Office Action issued in related Japanese Appln. No. 2008-516071 (dated Jul. 5, 2011) w/English translation.
Supplemental EP Search Report issued in related EP Appln. No. 06752607.9 (dated Oct. 20, 2011).
Communication dated May 24, 2013 in European Application No. 06 752 607.9 (5 pages).
Communication dated Mar. 25, 2014 in European Application No. 06 752 607.9 (4 pages).
Office Action dated Jul. 10, 2012 in corresponding Japanese Application No. 2008-516071 (with translation).

* cited by examiner

METHODS AND APPARATUS FOR CONTROLLING MASK LEAK IN CPAP TREATMENT

This application is a continuation of U.S. application Ser. No. 11/921,753, filed Dec. 7, 2007, now U.S. Pat. No. 8,789,526, which is the U.S. national phase of International Application No. PCT/AU2006/000823, filed Jun. 14, 2006 which designated the U.S. and claims priority to Australian Application No. AU2006900774, filed Feb. 16, 2006, Australian Application No. AU2005903089, filed Jun. 14, 2005, Australian Application No. 2005906122, filed Nov. 4, 2005, and Australian Application No. 2005906193, filed Nov. 8, 2005, each of which is incorporated herein by reference in its entirety.

BACKGROUND OF THE INVENTION

1. Field of the Invention

This invention relates to mechanical ventilation of sleep disordered breathing (5DB), and in particular to methods and apparatus for improving patient compliance in Continuous Positive Airway Pressure (CPAP) treatment.

2. Description of Related Art

A comprehensive background discussion of mechanical ventilation can be found in "Principles and Practice of Mechanical Ventilation" (1994) edited by Martin J Tobin, published by McGraw-Hill Inc., ISBN 0-07-064943-7.

The use of nasal Continuous Positive Airway Pressure (CPAP) to treat Obstructive Sleep Apnea (OSA) was invented by Cohn Sullivan, see U.S. Pat. No. 4,944,310. Generally, the treatment involves providing a supply of air or breathable gas from a blower to a patient via an air delivery conduit and a patient interface, such as a full-face or nasal mask, or nasal prongs. While treatment is effective, some patients find it uncomfortable. Improving patient comfort and compliance is a continuing challenge.

One way to improve comfort is to provide a more comfortable patient interface. In this regard, the ResMed MIRAGE™ masks have provided significant improvement in comfort. See U.S. Pat. Nos. 6,112,746; 6,357,441; 6,581, 602; and 6,634,358. A more recent development is the ResMed MIRAGE™ ACTIVA™ mask series. See International Patent Application WO 2001/97893.

In the early days of nasal CPAP systems for treating OSA, patients were first titrated in a clinical study to determine an optimal treatment pressure. Titration involves a patient sleeping overnight in a clinic and being tested with a mask and CPAP device. The treatment pressure provided by the CPAP device is adjusted until apneas are eliminated. The treatment pressure is usually in the range of 4-20 cmH$_2$O. A device would be set to that pressure and given to the patient to take home. A subsequent development was the automatically adjusting device that a patient could take home. The automatically adjusting device will raise and/or lower the treatment pressure based on indications of obstructive sleep apnea, such as snoring. Such CPAP devices are sometime generically referred to as Automatic Positive Airway Pressure (APAP) devices. See U.S. Pat. Nos. 5,245,995; 6,398, 739; and 6,635,021.

Another type of nasal CPAP device provides a first pressure during inhalation (sometimes termed an IPAP) and a second, lower pressure during exhalation (sometimes termed an EPAP). Examples of these include the ResMed VPAP™ series, and the Respironics BiPAP series. Bilevel CPAP devices may be prescribed for patients who do not comply with single pressure CPAP devices. Some patients perceive that the lower pressure during exhalation is more comfortable, at least while they are awake.

Another way of improving patient comfort and compliance is to start each therapy session at a low therapeutic pressure, e.g., 4 cmH$_2$O, and ramp up to fill therapeutic pressure over the first hour, to allow the patient to adjust to the sensation while falling asleep. Alternatively, the device may set to implement a time delay before fill therapeutic pressure is applied, to allow the patient time to fall asleep before full therapeutic pressure is applied. See U.S. Pat. Nos. 5,199,424 and 5,522,382.

Another form of automatically adjusting CPAP device is the ResMed AUTOSET™ SPIRIT™ device. In this device, the CPAP pressure is automatically increased or decreased in accordance with indications of flow limitation, such as flow flattening, snore, apnea and hypopnea. See U.S. Pat. Nos. 5,704,345; 6,029,665; 6,138,675; and 6,363,933. An advantage of an automatically adjusting system is that over time the treatment pressure required may vary for a particular patient and a correctly functioning automatic system can obviate the need for the patient to return for a subsequent sleep study. These patents also describe a method and apparatus for distinguishing between so-called "central" and obstructive apneas.

The contents of all of the aforesaid patents are incorporated by cross-reference.

Some OSA patients find treatment with the above devices uncomfortable and they become non-compliant with the therapy. Other patients such as cardiovascular patients with Congestive Heart Failure, patients with REM Hypoventilation, and patients with Respiratory Insufficiency could also benefit from a more comfortable and/or effective form of therapy.

One hurdle to patient acceptance of the therapy is in the initial fitting of the patient interface (e.g., mask), where the mask fit is tested under relatively low pressure and high flow. This may result in noisy operation of the device and high flow air leaks as the mask is adjusted to the patient, which can be a noisy and unsettling initial experience for the patient.

Another impediment to patient comfort and compliance may be the patient or bed partner being disturbed by air leaks from the mask.

SUMMARY OF THE INVENTION

One aspect of the invention relates to a method and apparatus to overcome or ameliorate one or more of these disadvantages.

Mask Leak Control

A first aspect of the invention relates to a method of operating a device for treating sleep disordered breathing (SDB), wherein said device provides continuous positive airway pressure during sleep, the method comprising:
  determining whether treatment pressure at the patient interface is below a desired value;
  in response to said determining, increasing pressure generated by the flow generator;
  in response to said increasing, making a determination that the increase in flow generator pressure has resulted in less than a desired increase in treatment pressure at the patient interface; and
  in response to said determination, reducing or inhibiting further increase of the flow generator pressure.

A further aspect of the invention relates to a method of operating a device for treating sleep disordered breathing (SDB), wherein said device provides continuous positive airway pressure during sleep, the method comprising:

determining whether treatment pressure at the patient interface is below a desired value;

in response to said determining, increasing pressure generated by the flow generator;

in response to said increasing, making a determination that the increase in flow generator pressure has resulted in a greater than desired increase in air leak from the patient interface, or has increased the air leak from the patient interface; and in response to said determination, reducing or inhibiting further increase of the flow generator pressure.

In one form, making a determination is made by comparison of a mask leak parameter to a mask leak threshold. The mask leak parameter may be a mask leak impedance parameter.

In an embodiment, the mask leak threshold is determined with reference to a patient arousal index, such as an Apnea Hypopnea Index (AHI), and/or a sleep phase index of the patient.

A further aspect of the invention relates to a method of operating a device for treating sleep disordered breathing (SDB), wherein said device provides continuous positive airway pressure during sleep, the method comprising:

comparing a mask leak parameter to a mask leak threshold to determine excessive leak at the patient interface;

in response to said determination of excessive leak, reducing the flow generator pressure; and continuing to compare said mask leak parameter to said mask leak threshold at said reduced flow generator pressure.

In an embodiment, the mask leak parameter is a mask leak impedance parameter.

In one embodiment, reducing the flow generator pressure includes reducing the pressure to a ramp start pressure, and the method further includes ramping up the pressure to a treatment pressure over a predetermined ramp time while continuing to compare the mask leak parameter to the mask leak threshold.

The method may further include halting the pressure ramping upon further determination of excessive leak at the patient interface.

In another embodiment, reducing the pressure includes reducing the pressure by a pressure increment to a first reduced pressure, and optionally incrementally further reducing the pressure if excessive leak is detected at the first reduced pressure.

A further aspect of the invention relates to a method of assessing the fit of a patient interface (e.g., a mask) to a patient for a device for treating sleep disordered breathing (SDB), wherein said device provides continuous positive airway pressure during sleep, the method comprising:

generating a treatment pressure at a flow generator of the device;

limiting gas flow applied to the patient to a predetermined flow rate;

determining that treatment pressure at the patient interface is below a desired value; and making a determination that the seal of the patient interface to the patient is inadequate.

In an embodiment, the flow rate is determined with reference to a vent flow rate of the patient interface.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

Hardware

A positive airway pressure (PAP) device in accordance with an embodiment of the invention includes a blower and blower-controller. The blower can deliver a supply of air at positive pressure 2-40 cmH$_2$O, but generally in the range of 4-20 cmH$_2$O to a patient interface via an air delivery conduit.

The device also includes a flow sensor to measure the flow of air along the conduit, and pressure sensors to measure the pressure of air at the blower outlet.

In one form, the device alternatively includes an additional pressure sensor to detect the pressure in the patient interface.

Figure 1:
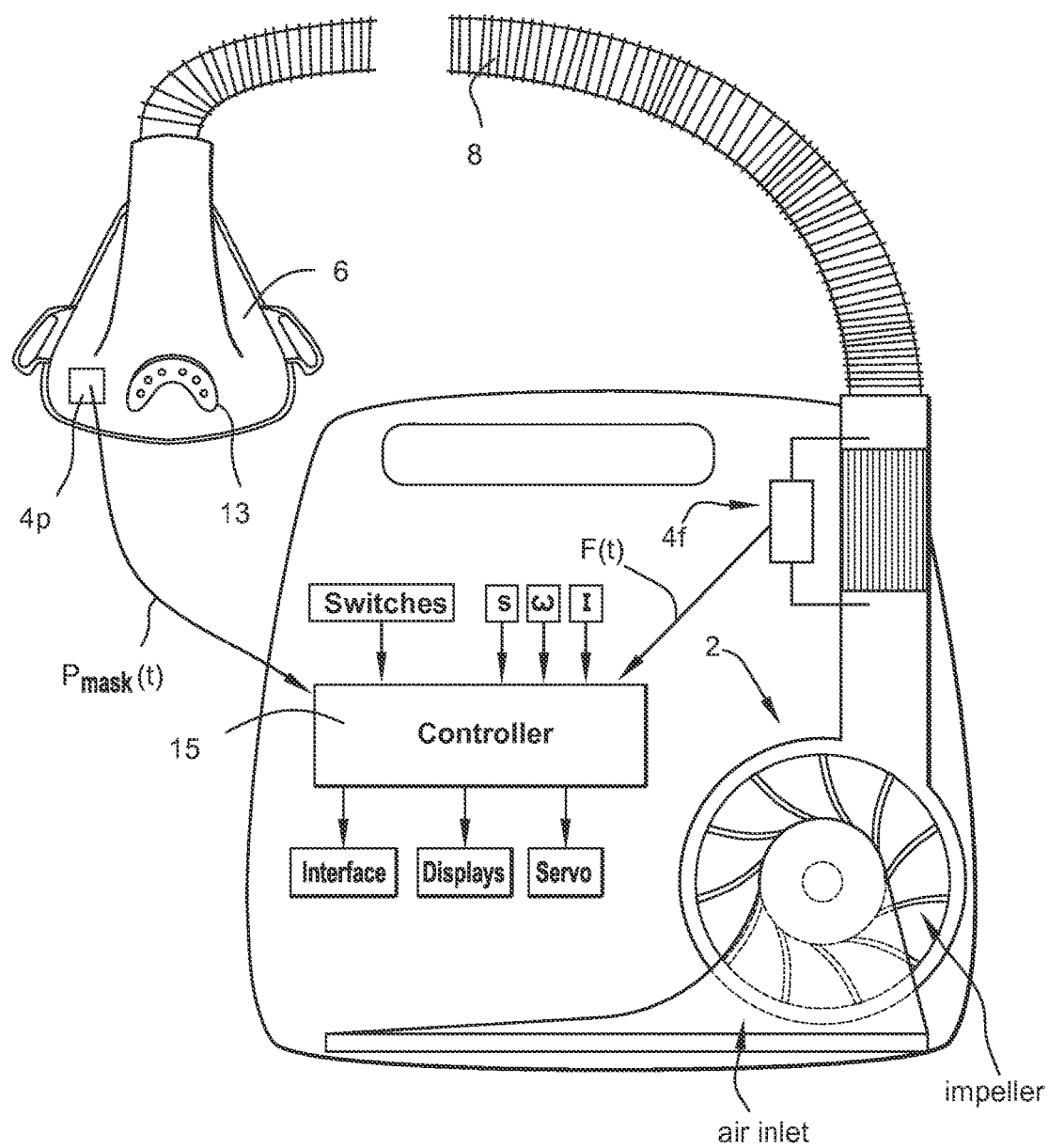
FIG. 1 illustrates a ventilator apparatus according to an embodiment of the present invention for implementing methods according to embodiments of the invention.

For example, FIG. 1 illustrates a ventilator device according to an embodiment of the invention. As illustrated, the ventilator device may include a servo-controlled blower 2, a flow sensor 4$f$, pressure sensor 4$p$, a mask 6, and an air delivery conduit 8 for connection between the blower 2 and the mask 6. Exhaust gas is vented via exhaust 13.

Mask flow may be measured by a flow sensor, such as a pneumotachograph and differential pressure transducer to derive a flow signal F(t). Alternatively, the pneumotachograph may be replaced by a bundle of small tubes aligned in parallel with the flow from the blower with the pressure difference measured by the differential pressure transducer across the bundle.

Mask pressure is preferably measured at a pressure tap using a pressure transducer to derive a pressure signal $P_{mask}(t)$. The pressure sensor 4$p$ and flow sensor 4$f$ have been shown only symbolically in FIG. 1 since it is understood that those skilled in the art would understand how to measure flow and pressure.

Flow F(t) and pressure $P_{mask}(t)$ signals are sent to a controller or microprocessor-referred to herein as processor 15—to derive a pressure request signal $P_{Request}(t)$. The controller or processor is configured and adapted to perform the methodology described in more detail herein. The controller or processor may include integrated chips, a memory and/or other instruction or data storage medium to implement the control methodology. For example, programmed instructions with the control methodology are either coded on integrated chips in the memory of the device or loaded as software. As those skilled in the art will recognize, analogue devices may also be implemented in the control apparatus.

The controller or processor 15 is further adapted to derive parameters indicative of the patient's breathing and sleep pattern, such as for deriving indications of flow limitation, such as flow flattening, snore, apnea and hypopnea and the Apnea Hypopnea Index (AHI), and for distinguishing between REM and non-REM sleep. See U.S. Pat. Nos. 5,704,345 and 6,029,665.

The apparatus of FIG. 1 includes other sensors, communication interfaces and displays, a servo, etc., and functional blocks the details of which are not necessary for an understanding of the present invention.

In an embodiment, the controller may be programmable by the clinician using the menu system to alter the parameters of the 'first timer' mode, for example, to set the initial therapy session pressure and/or the daily pressure increment according to the severity of the patient's sleep disordered breathing and the clinician's opinion of how long the patient may take to acclimatize to the sensations of the CPAP therapy.

At the commencement of the therapy session, the session timer of the controller is started.

Where the flow generator is of the type which provides for this, and where this feature is selected, the treatment pressure is ramped up over a 5 to 20 minute period at the beginning of each treatment session, starting at a low pressure, for example 4 cmH$_2$O, and ramps up to the desired full therapeutic pressure for the therapy session.

Mask Leak Control

In an embodiment of the invention, described with reference to FIGS. 2 and 3, the response of the blower to changes indicative of excessive air leakage at the patient interface is controlled for improved patient comfort and compliance and reduced possibility of disturbance.

Figure 2:
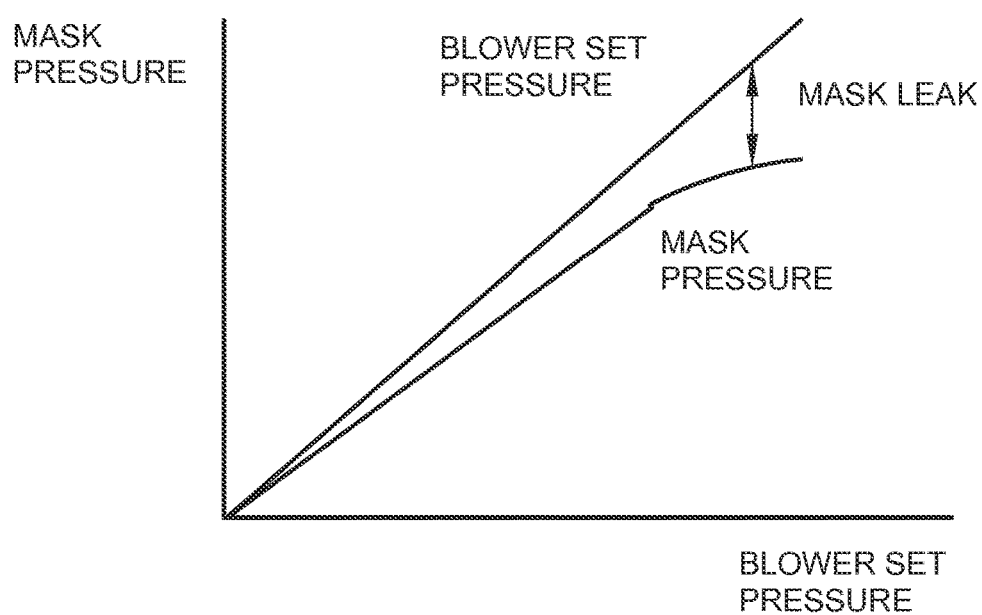
FIG. 2 is a graph of a mask pressure against blower set pressure, showing mask leak.

FIG. 2 is a schematic graph of mask pressure against flow generator pressure illustrating mask leak where the mask is not sitting properly and sealing completely on the patient's face, for example where the mask and headgear has not been optimally adjusted or where the patient may have partially dislodged the mask during sleep.

With reference to FIG. 2, the blower set pressure is on the x axis and the mask pressure on they axis.

It can be seen that the pressure lost due to the mask leak is the vertical distance between the mask pressure curve and the 45° line. In a typical situation, the mask leak at lower blower pressures will be approximately linear with blower pressure, but above a certain blower pressure will begin to depart more significantly from the blower pressure as the increased pressure and flow causes a significant increase in mask leakage. The point at which this departure commences, and the gradient of this departure, will depend on the type and fit of the mask to the patient, and may also vary from one session to the next, or within a therapy session, depending on the patient's sleeping position.

In prior art APAP machines, air leakage at the mask is detected by a drop in the pressure at the nasal interface, and the response of the blower as governed by the controller is to increase the blower pressure to compensate for the leak and thus maintain adequate treatment pressures to normalize the patient's AHI. However, in some instances this increased pressure merely serves to further reduce the sealing of the mask onto the patient's face, and the increased pressure is wholly or largely lost by increased leakage. In such instances, the volume of air being leaked is increased with little or no net benefit to efficacy of the therapy, and with increased chance of arousal of or disturbance to the patient and/or the bed partner.

In the present embodiment of the invention, the response of the blower to detection of mask leak is modified.

Figure 3:
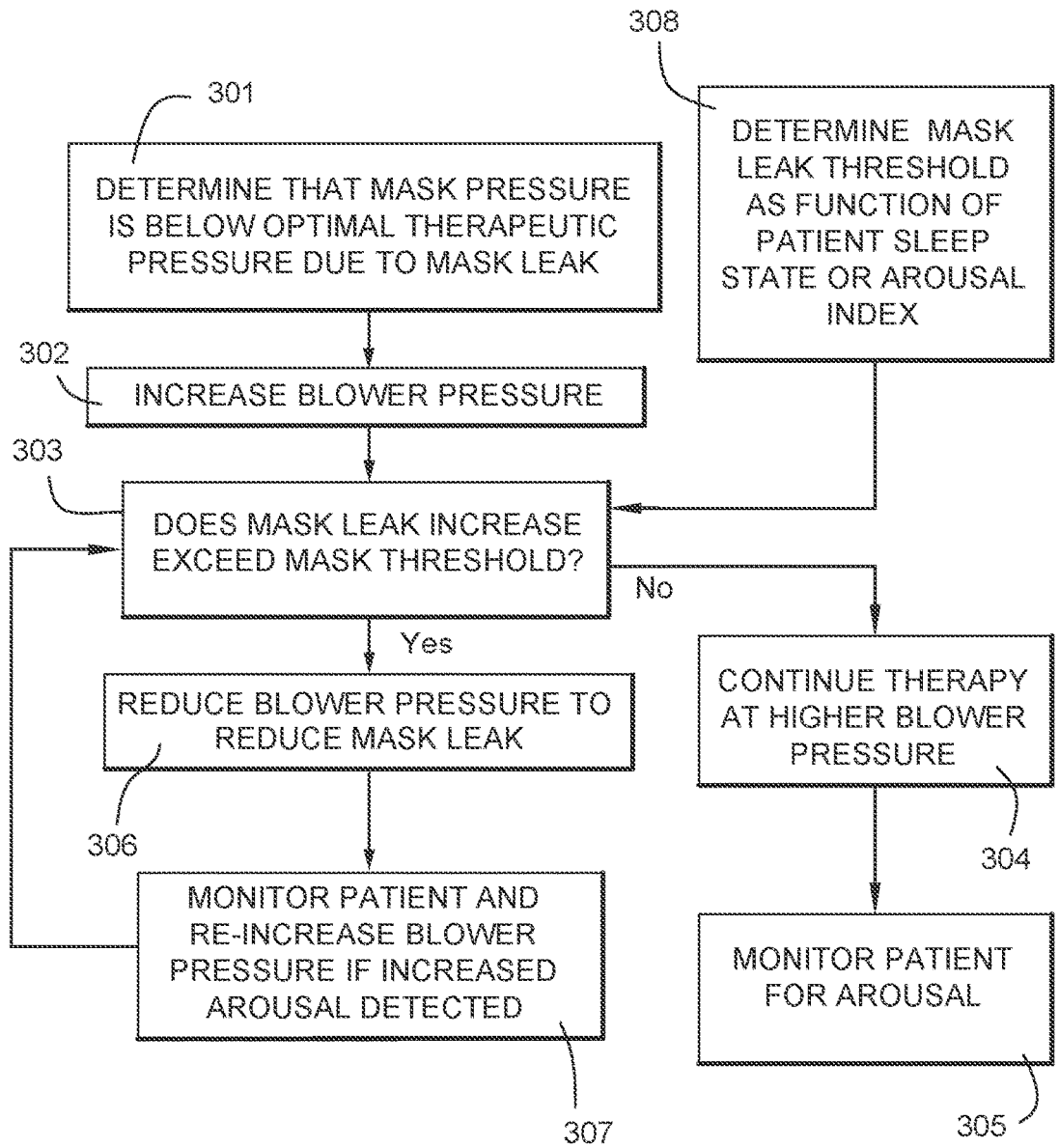
FIG. 3 is a flowchart illustrating mask leak control according to an embodiment of the invention.

FIG. 3 is a flowchart illustrating the steps of the mask leak control method according to an embodiment of the invention.

At first detection of excessive mask leak (step 301), for example as determined by low mask pressure, by an excessive differential between the blower pressure and the pressure at the mask or by a computed mask leak impedance parameter below a certain threshold, the blower controller causes an increase in the blower pressure (step 302) to compensate for the leak and maintain the therapeutic pressure to desired levels, thus moving further to the right along the mask pressure curve of FIG. 2.

Another determination of mask pressure is made (step 303) and, if the increased blower pressure has corrected the mask pressure to compensate for the leakage then the higher blower pressure is continued (step 304). The patient continues to be monitored for arousal (step 305).

If however the increased blower pressure has resulted in less than a predetermined pressure increase in the mask, or a greater than predetermined flow volume increase, this means that the blower is operating at a low-gradient part of the mask pressure curve of FIG. 2. In this case, the controller is programmed to then recognize that the pressure increase has wholly, or mostly, been ineffectual due to increased leakage at the mask.

When detecting this condition, the controller is programmed to then reduce the blower pressure (step 306) (for example, by a set percentage of the treatment pressure or to the ramp start pressure) or to inhibit further increases in the flow generator output pressure.

The mask leak threshold against which the increased mask leak is compared (step 308) may be a fixed quantity or proportion, for example where a 2 cmH$_2$O increase in blower results in less than a 1 cmH$_2$O pressure increase at the mask.

Alternatively, the mask leak threshold may vary as a function of a patient sleep phase indicator so that a greater amount of mask leakage is tolerated if the patient is in a heavier phase of sleep and thus less likely to be disturbed, or if other indicators of disturbance of the patient—such as respiratory rate—remain low. Indicators of sleep phase are known per se in sleep medicine and include monitoring of brain waves and/or respiration.

In a further alternative form of this embodiment, the mask leak threshold may vary as a function of indications of flow limitation, such as flow flattening, snore, apnea and hypopnea, or the Apnea Hypopnea Index (AHI), so that a greater amount of mask leakage is tolerated if the patient is more in need of higher treatment pressure. The blower controller is preferably programmable by the clinician to adjust the mask leak threshold, or turn off the mask leak control function, for patients with historically high flow limitation measurements.

By reducing the response of the flow generator to mask leak to operate the apparatus at a lower mask leak portion of the mask pressure/flow generator pressure curve of FIG. 2, the amount of flow generator energy wasted in producing undesirable outcomes of unwanted mask leak and noise is minimized.

By reducing or capping the blower set pressure in circumstances of high mask leakage, rather than increasing the pressure further as was done in the prior art, disturbance of the patient and/or bed partner by the noise or air flow caused by excessive air leakage is minimized. While the therapy may continue at sub-optimal pressure, it may continue to provide some airway support and is considered that this may in many instances be preferable to waking the patient or having the patient remove the mask during sleep. The former is a substantial patient comfort and compliance issue and the latter may deny the patient the entire benefit of the therapy. It is expected that, by reducing patient arousals, total sleep time and adherence to the treatment can be improved.

Furthermore, by reducing the blower set pressure in response to excessive mask leak, the mask may settle back into improved conformity with the patient's face and the mask leakage be reduced, thus altering the mask pressure curve shown in FIG. 2 to one closer to the 45° line.

The controller may be programmed to make one or more further attempts to ramp up blower pressure after a predetermined time periods, for example 15 minutes, have elapsed to reassess the quality of the mask-to-patient seal.

The controller may also be programmed to monitor in real time the patient's AHI and other patient arousal and flow limitation indicators, to detect any reduction in effectiveness of therapy at the lower pressure. If the indicators show increased flow limitation and/or patient arousal at the lower treatment pressure, indicative of insufficient treatment pressure for airway stability, the controller will re-increase the blower pressure (step 307).

Patient arousal may also be sensed by monitoring body position. Continual movement, if detected in conjunction with high leak, may indicate patient arousal due to mask leak.

Snoring is indicative of airway narrowing, and may be used as an indicator that the treatment pressure is too low and must be increased regardless of leak.

In essence, this embodiment seeks to apply the lowest pressure required to treat the patient effectively and limits maximum pressure in circumstances of mask leak, whereas previous treatments did only the former. In this way, a balance is achieved between patient arousal due to mask leak and effectiveness of the treatment, to help maintain patient compliance with the therapy.

The controller keeps a record of incidents where the blower pressure is reduced in response to excessive mask leak, for subsequent review by the clinician to help with mask selection and adjustment for the patient.

Also, at the end of a session where excessive mask leak has been detected, the controller may cause to be displayed on the machine a message alerting the patient to the need to adjust the fit of the mask, and/or to contact the clinician.

The CPAP machine may have one or more leak control modes. If the CPAP machine comprises a plurality of modes a control system may control selecting between these modes depending for example on patient preference and compliance levels. In a first of these modes, which for example may be selected for less compliant patients, the machine on detection of a leak reduces the treatment flow/pressure and maintains the pressure at a level below full-therapeutic to allow the mask to seal against the patient's face.

In the second mode of the leak control method, the flow/pressure is reduced to a sub-therapeutic pressure for a brief predetermined period, for example 15-60 seconds, to allow the mask to reseal against the patient's face, and then is ramped back up to therapeutic pressure. For example, upon detection of mask leak in excess of the mask leak threshold, the pressure may be reduced to the ramp start pressure used for the commencement of the therapy session, and then ramped back up to full therapeutic pressure over a shortened ramp time, such as 50% of the ramp time used at the commencement of therapy.

In a further mode, upon detection of mask leak in excess of the mask leak threshold, the pressure may be reduced by a set increment, e.g., by 1 $cmH_2O$, and the mask leak parameter is measured again for a set period of time. If the leak remains above the threshold, the pressure is further incrementally reduced, the mask leak measured again, and so on until the leak has been corrected or fallen below the mask leak threshold.

After a predetermined period of operation below the mask leak threshold, the controller re-increases the flow generator pressure to re-assess the mask-to-patient seal, as previously discussed.

In a further embodiment, a mask seal testing and mask fitting regimen is provided wherein the mask is fitted to the patient in a clinical setting and the device switched to a "mask fitting" operational mode. In this mode, the flow generator is controlled to apply a normal range treatment pressure, with the flow rate limited to a flow approximately equal to or slightly above the vent flow rate for the mask.

If the mask seals well, the pressure at the mask will be at or near full therapeutic pressure. If there is a substantial mask leak, this may be detected by insufficient pressure in the mask, without the noisy operation and large volume air leaks which the prior art low pressure-high volume mask fitting modes regimens. In this way, the mask fit may be adjusted without undue noise and a large volume of air flow rushing past the patient's face, and a further hurdle to patient adoption of and compliance with the therapy is reduced.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise, comprised and comprises where they appear.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. An apparatus configured for sealed delivery of a flow of breathable gas at a continuously positive pressure with respect to ambient air pressure to an entrance of a patient's airways including at least an entrance of the patient's nares while the patient is sleeping to treat sleep disordered breathing (SDB), the apparatus comprising:
   a blower configured to generate and pressurize the flow of breathable gas; and
   a controller configured to (1) adjust the blower to increase the pressure of the breathable gas when a treatment pressure is below a predetermined threshold, (2) determine whether the increase in the pressure of the breathable gas resulting from the adjustment of the blower is less than a predetermined increase in the treatment pressure and (3) generate the flow of breathable gas at a reduced positive pressure or inhibit a further increase in the pressure of the breathable gas when the increase in pressure resulting from the adjustment of the blower is less than the predetermined increase in the treatment pressure.

2. The apparatus according to claim 1, wherein the controller is configured to adjust the blower based on a comparison between a leak parameter and a leak threshold.

3. The apparatus according to claim 2, wherein the leak parameter is a mask leak impedance parameter.

4. The apparatus according to claim 2, wherein the leak threshold is based on a patient arousal index.

5. The apparatus according to claim 4, wherein the patient arousal index includes at least one of an Apnea Hypopnea Index (AHI) and a sleep phase index of the patient.

6. The apparatus according to claim 5, wherein the sleep phase index is based on at least one of: brain waves of the patient and respiration of the patient.

7. The apparatus according to claim 5, wherein the patient arousal index is based on body position.

8. The apparatus according to claim 5, wherein the patient arousal index is based on snoring.

9. The apparatus according to claim 2, wherein the leak threshold varies as a function of indications of a flow limitation.

10. The apparatus according to claim 9, wherein the indications of a flow limitation include flow flattening, snore, apnea, hypopnea, and/or Apnea Hypopnea Index (AHI).

11. The apparatus according to claim 2, wherein the controller is configured to adjust the leak threshold or turn off a leak control function.

12. The apparatus according to claim 2, wherein the controller is configured to maintain a record of incidents where the blower is adjusted to reduce the pressure of the breathable gas in response to an excessive leak for subsequent review by a clinician to facilitate patient interface selection and/or adjustment for the patient.

13. The apparatus according to claim 2, wherein the controller is configured to operate in one or more leak control modes.

14. The apparatus according to claim 13, wherein the one or more leak control modes are selectable depending on patient preference and/or compliance levels.

15. The apparatus according to claim 13, wherein the one or more leak control modes includes a first mode in which the controller adjusts the blower to reduce the pressure of the breathable gas upon detection of a leak and maintain the pressure of the breathable gas at a level below a full-therapeutic pressure to allow a patient interface to seal against the patient's face.

16. The apparatus according to claim 13, wherein the one or more leak control modes includes a second mode in which the controller adjusts the blower to reduce the pressure of the breathable gas to a sub-therapeutic pressure for a brief predetermined period to allow a patient interface to reseal against the patient's face, and then ramp back up to a full-therapeutic pressure.

17. The apparatus according to claim 16, wherein the brief predetermined period is 15-60 seconds.

18. The apparatus according to claim 13, wherein the one or more leak control modes includes a third mode in which the controller adjusts the blower to reduce the pressure of the breathable gas upon detection of a leak in excess of the leak threshold to a ramp start pressure used for commencement of a therapy session, and then ramp back up to full therapeutic pressure over a shortened ramp time.

19. The apparatus according to claim 18, wherein the shortened ramp time is 50% of a ramp time used at the commencement of the therapy session.

20. The apparatus according to claim 13, wherein the one or more leak control modes includes a fourth mode in which the controller adjusts the blower to reduce the pressure of the breathable gas by a set increment upon detection of a leak in excess of the leak threshold, measure the leak parameter for a set period of time, and further incrementally reduce the pressure of the breathable gas if the leak remains above the leak threshold.

21. The apparatus according to claim 20, wherein the set increment is 1 cmH$_2$O.

22. The apparatus according to claim 2, wherein the controller is configured to adjust the blower to re-increase the pressure of the breathable gas to re-assess a patient interface-to-patient seal after a predetermined period of operation below the leak threshold.

23. The apparatus according to claim 1, wherein the apparatus further comprises:
a patient interface configured to sealingly engage the patient's face; and
an air delivery tube fluidly connected to the blower and configured to deliver the pressurized breathable gas to the patient interface.

24. The apparatus according to claim 23, wherein the controller is configured to operate in a patient interface fitting operational mode in which the controller controls the blower to apply a normal range treatment pressure in order to perform a patient interface seal testing and patient interface fitting regimen and fit the patient interface to the patient in a clinical setting.

25. The apparatus according to claim 24, wherein the controller is configured to adjust the blower to limit a flow rate of the breathable gas to a flow approximately equal to or slightly above a vent flow rate for the patient interface.

26. The apparatus according to claim 23, wherein the controller is configured to adjust the blower to maintain a therapy pressure at the patient interface in a range of about 2 cmH$_2$O to about 40 cmH$_2$O above ambient air pressure.

27. The apparatus according to claim 23, further comprising a pressure sensor configured to detect a pressure of the breathable gas at the patient interface.

28. The apparatus according to claim 23, wherein said less than a predetermined increase in the treatment pressure is indicative of a greater than desired gas leak or increase in gas leak at the patient interface.

29. The apparatus according to claim 1, further comprising a flow sensor positioned downstream of the blower, the flow sensor being configured to detect a flow rate of the pressurized breathable gas provided by the blower.

30. The apparatus of claim 1, wherein the reduced positive pressure is sufficient to provide airway support to the patient during sleep disordered breathing therapy.

31. An apparatus configured for sealed delivery of a flow of breathable gas at a continuously positive pressure with respect to ambient air pressure to an entrance of a patient's airways including at least an entrance of the patient's nares while the patient is sleeping to treat sleep disordered breathing (SDB), the apparatus comprising:
a blower configured to generate and pressurize the flow of breathable gas; and
a controller configured to (1) compare a leak parameter to a leak threshold to determine an excessive leak, (2) adjust the blower to generate the flow of pressurized breathable gas at a reduced positive pressure when the controller determines that there is an excessive leak, and (3) continue comparing said leak parameter to said leak threshold at said reduced breathable gas pressure,
wherein the reduced positive pressure is within a range of treatment pressures that provide airway support to the patient during sleep disordered breathing therapy.

32. The apparatus according to claim 31, wherein the leak parameter is a mask leak impedance parameter.

33. The apparatus according to claim 31, wherein the controller is configured to adjust the blower to generate and pressurize the flow of breathable gas at a ramp start pressure when the controller determines that there is an excessive leak.

34. The apparatus according to claim 33, wherein the controller is configured to adjust the blower to ramp up the pressure of the breathable gas within the range of treatment pressures over a predetermined ramp time while continuing to compare the leak parameter to the leak threshold.

35. The apparatus according to claim 34, wherein the controller is configured to adjust the blower to halt the pressure ramping upon further determination of the excessive leak.

36. The apparatus according to claim 31, wherein the controller is configured to adjust the blower to incrementally reduce the pressure of the breathable gas to the reduced positive pressure.

37. The apparatus according to claim 36, wherein the controller is configured to adjust the blower to generate the flow of pressurized breathable gas at a further reduced positive pressure in response to a detection of excessive leakage at the reduced positive pressure.

38. The apparatus according to claim 31, wherein the apparatus further comprises:
   a patient interface configured to sealingly engage the patient's face; and
   an air delivery tube fluidly connected to the blower and configured to deliver the pressurized breathable gas to the patient interface.

39. The apparatus of claim 31, wherein the controller is configured to operate in a plurality of leak control modes based on inputted patient compliance levels.

40. An apparatus configured for sealed delivery of a flow of breathable gas at a continuously positive pressure with respect to ambient air pressure to an entrance of a patient's airways including at least an entrance of the patient's nares while the patient is sleeping to treat sleep disordered breathing (SDB), the apparatus comprising:
   a blower configured to generate and pressurize the flow of breathable gas; and
   a controller configured to (1) adjust the blower to generate a treatment pressure, (2) adjust the blower to limit gas flow applied to the patient to a target flow rate and (3) determine that a seal between a patient interface and the patient's face is insufficient based on the treatment pressure at the patient interface being below a predetermined value,
   wherein the controller is further configured to decrease the treatment pressure upon the determination that the seal between the patient interface and the patient's face is insufficient, the decreased treatment pressure being sufficient to provide airway support to the patient during sleep disordered breathing therapy.

41. The apparatus according to claim 40, wherein the target flow rate is based on a vent flow rate of the patient interface.

42. The apparatus according to claim 40 further comprising:
   the patient interface; and
   an air delivery tube fluidly connecting the blower to the patient interface.

* * * * *